(12) United States Patent
Larsen

(10) Patent No.: US 8,028,566 B2
(45) Date of Patent: Oct. 4, 2011

(54) DUAL SAMPLE CARTRIDGE AND METHOD FOR CHARACTERIZING PARTICLES IN LIQUID

(75) Inventor: Ulrik Darling Larsen, Lyngby (DK)

(73) Assignee: Chempaq A/S, Farum (DK)

( * ) Notice: Subject to any disclaimer, the term of this patent is extended or adjusted under 35 U.S.C. 154(b) by 927 days.

(21) Appl. No.: 11/815,884

(22) PCT Filed: Feb. 10, 2006

(86) PCT No.: PCT/DK2006/000080
§ 371 (c)(1),
(2), (4) Date: Sep. 13, 2007

(87) PCT Pub. No.: WO2006/084472
PCT Pub. Date: Aug. 17, 2006

(65) Prior Publication Data
US 2008/0202217 A1     Aug. 28, 2008

Related U.S. Application Data

(60) Provisional application No. 60/655,416, filed on Feb. 24, 2005.

(30) Foreign Application Priority Data

Feb. 10, 2005 (DK) ................................ 2005 00199

(51) Int. Cl.
*G01N 15/06* (2006.01)
(52) U.S. Cl. .................................................... 73/61.71
(58) Field of Classification Search ............... 73/61.71
See application file for complete search history.

(56) References Cited

U.S. PATENT DOCUMENTS

| | | |
|---|---|---|
| 2,656,508 A | 10/1953 | Coulter |
| 3,122,431 A | 2/1964 | Coulter et al. |
| 3,395,343 A | 7/1968 | Morgan et al. |
| 3,549,994 A | 12/1970 | Rothermel et al. |
| 3,902,115 A | 8/1975 | Hogg et al. |
| 3,958,177 A | 5/1976 | Reeves et al. |
| 4,014,611 A | 3/1977 | Simpson et al. |
| 4,346,018 A | 8/1982 | Carter et al. |

(Continued)

FOREIGN PATENT DOCUMENTS

EP        0193394 A1    7/1991
(Continued)

OTHER PUBLICATIONS

Larsen, Ulrik. WO 03/104772 A1, Dec. 18, 2003.*

(Continued)

*Primary Examiner* — Hezron E Williams
*Assistant Examiner* — Paul West
(74) *Attorney, Agent, or Firm* — Volentine & Whitt, PLLC

(57) ABSTRACT

The present invention relates to an apparatus for characterizing particles suspended in a liquid, especially a self-contained disposable cartridge for single-use analysis, such as for single-use analysis of a small quantity of whole blood. Furthermore, the present invention relates to a method for characterizing particles in liquid and a device for sampling a small and accurate volume of liquid. The apparatus comprises a housing having a mixing chamber and a collection chamber separated by a wall containing an opening, a first bore in the outer surface of the housing for entrance of a liquid sample, a first cavity for receiving and holding a first liquid sample, and a second cavity for receiving and holding a second liquid sample.

30 Claims, 14 Drawing Sheets

U.S. PATENT DOCUMENTS

| | | | |
|---|---|---|---|
| 4,485,175 | A | 11/1984 | Ledis et al. |
| 4,521,129 | A | 6/1985 | Krech et al. |
| 4,521,729 | A | 6/1985 | Kiesewetter et al. |
| 4,528,274 | A | 7/1985 | Carter et al. |
| 4,600,880 | A | 7/1986 | Doutre et al. |
| 4,607,526 | A | 8/1986 | Bachenheimer et al. |
| 4,706,207 | A | 11/1987 | Hennessy et al. |
| 4,738,827 | A | 4/1988 | Pierotti |
| 4,745,071 | A | 5/1988 | Lapicola et al. |
| 4,751,179 | A | 6/1988 | Ledis et al. |
| 4,760,328 | A | 7/1988 | Groves |
| 4,835,457 | A | 5/1989 | Hanss et al. |
| 4,926,114 | A | 5/1990 | Doutre |
| 4,962,038 | A | 10/1990 | Carter et al. |
| 5,045,474 | A | 9/1991 | Becker et al. |
| 5,077,017 | A | 12/1991 | Gorin et al. |
| 5,104,813 | A | 4/1992 | Besemer et al. |
| 5,198,749 | A | 3/1993 | Guthrie et al. |
| 5,230,866 | A | 7/1993 | Shartle et al. |
| 5,231,005 | A | 7/1993 | Russell et al. |
| 5,241,262 | A | 8/1993 | Guthrie et al. |
| 5,257,984 | A | 11/1993 | Kelley |
| 5,316,951 | A | 5/1994 | Carver, Jr. et al. |
| 5,334,502 | A | 8/1994 | Sangha |
| 5,348,859 | A | 9/1994 | Brunhouse et al. |
| 5,393,496 | A | 2/1995 | Seymour |
| 5,500,992 | A | 3/1996 | Barnes et al. |
| 5,501,982 | A | 3/1996 | Saldivar, Jr. et al. |
| 5,623,200 | A | 4/1997 | Ogino |
| 5,716,852 | A | 2/1998 | Yager et al. |
| 5,731,206 | A | 3/1998 | Ledis et al. |
| 5,763,280 | A | 6/1998 | Li et al. |
| 5,804,022 | A | 9/1998 | Kaltenbach et al. |
| 5,834,315 | A | 11/1998 | Riesgo et al. |
| 5,840,515 | A | 11/1998 | Provost |
| 5,882,934 | A | 3/1999 | Li et al. |
| 5,911,871 | A | 6/1999 | Priess et al. |
| 5,979,251 | A | 11/1999 | James et al. |
| 6,111,398 | A | 8/2000 | Graham |
| 6,159,740 | A | 12/2000 | Hudson et al. |
| 6,230,896 | B1 | 5/2001 | Lambert |
| 6,251,615 | B1 | 6/2001 | Oberhardt |
| 6,319,209 | B1 | 11/2001 | Kriz |
| 6,387,328 | B1 | 5/2002 | Berndtsson |
| 6,663,833 | B1 | 12/2003 | Stave et al. |
| 6,852,284 | B1 * | 2/2005 | Holl et al. ............ 422/68.1 |

FOREIGN PATENT DOCUMENTS

| | | | |
|---|---|---|---|
| EP | 0549414 | A1 | 6/1993 |
| EP | 0844475 | A1 | 5/1998 |
| EP | 1182457 | A1 | 2/2002 |
| GB | 2232769 | A | 12/1990 |
| GR | 1002424 | B | 8/1996 |
| JP | 5915849 | A | 1/1984 |
| JP | 61205844 | | 9/1986 |
| JP | 7301595 | | 11/1995 |
| JP | 8015125 | | 1/1996 |
| JP | 9304265 | | 11/1997 |
| JP | 2002515601 | | 5/2002 |
| WO | 9301306 | A1 | 1/1993 |
| WO | 9724600 | A1 | 7/1997 |
| WO | 9850777 | A1 | 11/1998 |
| WO | 9854568 | A1 | 12/1998 |
| WO | 9901742 | | 1/1999 |
| WO | 9901742 | A1 | 1/1999 |
| WO | 9949319 | A1 | 9/1999 |
| WO | 9960379 | | 11/1999 |
| WO | 0007254 | A1 | 2/2000 |
| WO | 0111338 | A1 | 2/2001 |
| WO | 0169292 | A2 | 9/2001 |
| WO | 02089670 | A1 | 11/2002 |
| WO | 03044488 | | 5/2003 |
| WO | 03104772 | | 12/2003 |
| WO | 2004061411 | | 7/2004 |

OTHER PUBLICATIONS

Betancourt, Tomas. WO 2004/061411 A2, Jul. 22, 2004.*

Volker Kachel, "Electrical Resistance Pulse Sizing: Coulter Sizing", Flow Cytometry and Sorting, 2nd ed., pp. 45-80, 1990 Wiley-Liss Inc.

Ed. M.M. Wintrobe et al., "Clinical Hematology", pp. 3-9, 1981, 8th ed., Lea & Febiger, Philadelphia, USA.

M. Madou, "Fundamentals of Microfabrication", p. 39-32, 66-70, 145 and 163-164, CRC Press LLC,1997, ISBN 0-8493-9451-1.

A.Y. Fu et al., "A Microfabricated fluorescene-activated cell sorter", Nature Biotechnology, Vo. 17, Nov. 1999, pp. 1109-1111.

B.K. Gale et al., "Micromachined Electrical Field-Flow Fractionation (u-EFFFF) System", Proceedings of the IEEE Annual International Workshop; pp. 119-124; Jan. 1997.

* cited by examiner

DUAL SAMPLE CARTRIDGE AND METHOD FOR CHARACTERIZING PARTICLES IN LIQUID

CROSS REFERENCE TO RELATED APPLICATIONS

This application is the national phase under 35 U.S.C. 371 of PCT International Application No. PCT/DK2006/000080 which has an international filing date of Feb. 10, 2006, and also claims priority under 35 U.S.C. 119 to Danish application PA 2005 00199 filed on Feb. 10, 2005, and U.S. provisional application 60/655,416 filed on Feb. 24, 2005, all of which applications are hereby incorporated by reference in their entirety for all purposes as if fully set forth herein.

BACKGROUND OF THE INVENTION

1. Field of the Invention

The present invention relates to an apparatus for characterizing particles suspended in a liquid, especially a self-contained disposable cartridge for single-use analysis, such as for single-use analysis of a small quantity of whole blood.

2. Description of the Background Art

Present instruments for particle characterization such as counting and sizing are fairly expensive, immobile and require operation by trained personnel. The consequence hereof has been that many instruments are placed in dedicated laboratories that are operated by specialized personnel. Furthermore, the samples to be analyzed must be transported to this laboratory and the results are reported back to the requiree.

However, efforts have been made to provide a disposable cartridge for particle characterization. WO 03/104772 discloses a cartridge for analysis of a blood sample. The cartridge disclosed in WO 03/104772 can be used for determination of the content of haemoglobin and for counting and differentiation between three types of white blood cells (WBCs). In one embodiment the platelets are counted after lysing of the blood sample. In another embodiment the cartridge comprises two orifices and two mixing chambers for characterization of a blood sample. The blood sample is diluted in a first mixing chamber for particle characterization of WBCs through a first orifice and a part of the diluted sample is further diluted in a second mixing chamber for particle characterization of red blood cells (RBCs) and platelets (PLTs) through a second orifice.

WO 03/044488 discloses a disposable apparatus for use in blood testing, the apparatus being adapted for simultaneous dilution of blood into two different dilution ratios in two different mixing chambers.

SUMMARY OF THE INVENTION

It is an object of the present invention to provide an apparatus for a more accurate characterization of particles, e.g. platelets, RBCs and WBCs and their subpopulations, such as granulocytes, monocytes, and lymphocytes, in a liquid, such as blood.

It is another object of the present invention to provide an apparatus that has a simple flow system for counting of platelets and RBCs.

According to the present invention, the above-mentioned and other objects are fulfilled by an apparatus for characterizing particles in liquid, comprising a housing with a mixing chamber and a collection chamber separated by a wall containing an opening for the passage of the particles between the mixing chamber and the collection chamber. The housing may further comprise particle characterization means for characterizing particles passing through the opening, a first bore in the outer surface of the housing for entrance of liquid and a first cavity for receiving and holding a first liquid sample, the first cavity being movably positioned in relation to the housing in such a way that, in a first position, the first cavity is positioned for entrance of the first liquid sample into the first cavity, and, in a second position, the first cavity is in communication with the mixing chamber for discharge of the first liquid sample into the mixing chamber. The housing may further comprise a second cavity for receiving and holding a second liquid sample, the second cavity being movably positioned in relation to the housing in such a way that, in a first position, the second cavity is in communication with the first bore for entrance of the second liquid sample into the second cavity, and, in a second position, the second cavity is in communication with the mixing chamber for discharge of the second liquid sample into the mixing chamber.

Preferably, in their first positions, the first cavity, the second cavity and the first bore are connected in series for entrance of the first and second liquid samples into the first cavity and the second cavity, respectively. In the first positions of the cavities, a connecting channel may be provided to interconnect the first cavity and the second cavity.

Alternatively, in the first positions of the cavities, the first cavity and the second cavity may be connected in parallel with the first bore for entrance of the first and second liquid samples into the first cavity and the second cavity, respectively.

In a preferred embodiment, the first cavity is positioned in a first sampling member movably positioned in the housing, and the second cavity is positioned in a second sampling member movably positioned in the housing. In a first position of the second sampling member, i.e. a first position of the second cavity, the second cavity is in communication with the first bore. Preferably, in the first position of the second sampling member, the second cavity is in communication with a connecting channel, which, in the first position of the first sampling member, i.e. the first position of the first cavity, is in communication with the first cavity, such that the first bore, the first cavity in the first position, the connecting channel, and the second cavity in the first position form a channel for entrance of liquid into the first cavity and the second cavity. In a second position of the first sampling member and the second sampling member, the first cavity and/or the second cavity may be in communication with an inlet to the mixing chamber, respectively.

In another embodiment, the first cavity and the second cavity are positioned in a first sampling member that is movably positioned in the housing. In this embodiment, in the first position of the first sampling member, i.e. in the first positions of the first cavity and the second cavity, the first cavity and the second cavity are in communication with a connecting channel and the first bore in the outer surface of the housing for entrance of liquid, such that the first bore, the first cavity, the second cavity, and the connecting channel form a channel for entrance of liquid into the first and second cavity. In a second position of the first sampling member, i.e. a second position of the first cavity, the first cavity may be in communication with an inlet to the mixing chamber. In a third position of the first sampling member, i.e. a second position of the second cavity, the second cavity may be in communication with an inlet to the mixing chamber.

Preferably, the sampling member or members are rotatable about an axis of rotation that is substantially perpendicular to a longitudinal axis of their respective cavities.

Additionally or alternatively, the sampling member or members may be displaced in a direction substantially perpendicular to a longitudinal axis of one of the first and second cavity.

Preferably, the sampling member or members are made of a polymer.

The housing may further comprise a second bore in the outer surface of the housing for entrance of liquid. In the first position, the first cavity may be in communication with the second bore for entrance of the first liquid sample into the first cavity.

Thus, the first cavity and the second cavity in the first sampling member and/or second sampling member receive and hold first and second samples of precise volume of liquid, respectively, and the first sampling member and/or the second sampling member operate to transfer the first sample and the second sample to an inlet of the mixing chamber.

Preferably, liquid to be sampled enters the respective cavities by capillary attraction causing a liquid flow. Utilization of capillary forces simplifies the flow system, since no pumps, membranes, syringes or other flow generating means are needed to take the sample.

Thus, the first bore and/or second bore may form capillary tunnel(s) for entrance of liquid by capillary attraction. The capillary tunnel(s) is/are dimensioned so that, upon contact between the bore and liquid to be sampled, a sample of the liquid is drawn into the bore by capillary attraction.

Further, the first cavity may form a capillary tunnel adapted for drawing the liquid sample into the first cavity by capillary attraction, the second cavity may form a capillary tunnel adapted for drawing the liquid sample into the second cavity by capillary attraction, and the connecting channel may form a capillary tunnel adapted for drawing the liquid sample into the connecting channel by capillary attraction.

The capillary tunnels may together form a capillary tunnel.

Preferably, the first cavity and the second cavity are channels with different diameter, e.g. the second cavity has a larger diameter than the first cavity to enhance capillary effect when the first sampling member and/or the second sampling member are in their first positions. Further, it is preferred that the first cavity and the second cavity in their first positions extend along substantially the same longitudinal center axis.

The first and/or second sampling members may comprise at least one recess in their surface, such that the at least one recess and an abutting surface of the housing define the first cavity and/or the second cavity for receiving and holding first and/or second liquid samples.

Preferably, the first and second liquid samples have different volumes. Counting of platelets and RBCs usually requires a blood sample to be diluted in the range from about 1:2,000 to about 1:100,000, preferably about 1:10,000. Counting of WBCs after lysing of a blood sample usually requires a blood sample to be diluted in the range from about 1:100 to about 1:2,000, preferably 1:500. The different dilution ratios of the samples for counting of platelets/RBC and WBC, respectively, may be obtained by adjusting the volume of the sample and/or the volume of the liquid in one or more liquid storage chambers for dilution and further treatment of blood samples.

The surfaces of the inner capillary tunnel walls may be hydrophilic whereby the capillary attraction of the liquid sample is facilitated. For example, the inner tunnel walls may be made of e.g. glass or polymers, such as polystyrene.

Alternatively, the capillary tunnel walls may be made of another type of material and covalently or non-covalently coated with a hydrophilic material, such as a polymer or a reagent.

The first and/or second cavities may have an anti-coagulation reagent on its surface. Further, the capillary tunnels may also include one or more reagents adhered or chemically bonded to the inner tunnel walls. These reagents serve the purposes of further facilitating the capillary attraction of the sample and optionally also causing a chemical reaction in the liquid sample, e.g. introducing anticoagulant activity in a blood sample. Such reagents may comprise heparin, salts of EDTA, etc.

The volume of the first cavity and thus substantially the volume of the first sample may range from 0 to 10 μL, such as from 0.1 μL to 1 μL, preferably about 0.2 μL. The volume of the second cavity and thus substantially the volume of the second sample may range from 0 to 100 μL, such as from 0.5 μL to 10 μL, preferably about 2 μL.

The particle characterization means may include a first electrode in the mixing chamber and a second electrode in the collection chamber, each electrode being electrically connected to a respective terminal member accessible at the outer surface of the housing.

The housing may further comprise a first liquid storage chamber for holding liquid for first and/or second sample treatment. In the second position of the first cavity, the first cavity may be in communication with the first liquid storage chamber for flushing the first sample into the mixing chamber.

Additionally, the housing may comprise a second liquid storage chamber for holding liquid for first and/or second sample treatment. In the second position of the second cavity, the second cavity may be in communication with the first liquid storage chamber and/or the second liquid storage chamber for flushing the second sample into the mixing chamber.

Preferably, the first liquid storage chamber and the second liquid storage chamber are constructed to facilitate total draining of the chambers.

Preferably, the first liquid storage chamber and/or the second liquid storage chamber contain a diluent, e.g. water, or other liquids such as reagents, solvents, lysing agents or suitable solutions for sample treatment.

Preferably, the housing of the apparatus constitutes a cartridge for a single analysis of a dual sample blood portion.

In accordance with a further aspect of the invention, an apparatus is provided for characterizing particles suspended in a liquid, comprising a housing as disclosed herein constituting a cartridge, and a docking station for removably receiving the cartridge, the docking station comprising connectors for operational connection with the particle characterization means when the cartridge is received in the docking station.

The housing, e.g. constituting a cartridge, may further comprise a first port communicating with the mixing chamber for causing a liquid flow from the liquid storage chambers through the first cavity and the second cavity to the mixing chamber, and the docking station may further comprise a corresponding port for forming a gas connection with the first port when the cartridge is received in the docking station for application of a pressure causing a liquid flow through the first cavity and the second cavity. In one embodiment of the present invention, application of a pressure on the first port of the housing may cause a liquid flow through the opening.

Preferably, the housing further comprises a second port communicating with the collection chamber for causing a liquid flow through the opening, and the docking station may further comprise a corresponding port for forming a gas connection with the cartridge port when the housing is received in the docking station for application of a pressure causing a liquid flow through the opening. In one embodiment of the present invention, liquid flow through the opening may be obtained by application of a pressure on the first port of the housing.

One or more pistons or membranes may be integrated into the housing to include a source of pressure for causing a liquid flow in the housing. The docking station may provide a mechanical force for moving the one or more pistons or membranes. Furthermore, the docking station may be adapted to move, e.g. around an axis by rotating and/or along an axis by pushing and/or pulling, the first sampling member and/or the second sampling member into different positions, e.g. first positions, second positions and/or third positions.

The particle characterization means may include a first electrode in the mixing chamber and a second electrode in the collection chamber, each electrode being electrically connected to a respective terminal member accessible at the outer surface of the housing for operational connection to the respective connector of the docking station when the housing is received in the docking station. Generally, it is preferred that all necessary mechanical, electrical and fluid connections to the housing can be established by fitting the housing constituting a cartridge into the docking station, preferably by a simple push fit for simple insertion and removal of the housing.

The first and second electrodes may facilitate particle characterization utilizing the well-known Coulter impedance principle, e.g. for counting and sizing of blood cells. This method has become a globally accepted method and is being used in the majority of haematology-analysers. Several thousand particles per second may be characterized with high precision and accuracy utilizing this principle.

The opening in the wall between the mixing chamber and the collection chamber may be in the form of an orifice, a channel or a duct. Preferably, the opening is an orifice.

With the electrical impedance technique it is possible to resolve the particle volume from the measurement. By maintaining a constant current across the opening or orifice, the recorded voltage pulse from particles displacing the electrolyte in the orifice will have a height proportional to the volume of the particle. This is because particles can be considered non-conducting compared to the electrolyte, the electrical field (DC or RF) in the centre of the orifice is homogeneous, which is normally the case when the diameter D is smaller than the length I of the orifice (I/D>1), the particle d is to be considered small compared to the diameter of the orifice (d<0.2*D), only one particle passes through at a time, and the particles are passed through the orifice along the length of the orifice.

Normally such apparatus is operated so that the flow through the opening is into the collection chamber.

Preferably, the length of the orifice is from 1 µm to 1000 µm, for example about 50 µm. Desirably the length of the orifice is chosen such that only one particle will be present in the orifice at the time when detecting particles of from 0.1 µm to 100 µm diameter. However, considerations to the homogeneity of the electrical field in the orifice may require a length of the orifice larger or equal to the diameter. The counts, of which some may be simultaneous counting of two particles, can be corrected mathematically by implementing a statistical estimation. The aspect ratio of the orifice, (length or depth divided by diameter) is preferably from 0.5:1 to 5:1, more preferably from 1:1 to 3:1.

Preferably, the largest cross-sectional dimension of the orifice is from 5 µm to 200 µm, for example 10 µm to 50 µm.

Preferably, the wall between the mixing chamber and the collection chamber comprises a membrane with an orifice for passage of particles and/or liquid between the mixing chamber and the collection chamber.

As explained above, the present invention provides in preferred aspects a sensor based on a membrane fabricated in e.g. a polymer sheet. Orifice formation with high precision and high reproducibility can be fabricated by laser ablation. The membrane has an orifice placed relatively in the centre of the membrane, which can be used for aspiration of particles suspended in a liquid, as the sensor is submerged into the liquid. This way of transporting particles into a measuring region is known for electrical characterization of particles by the Coulter principle (V. Kachel, "Electrical Resistance Pulse Sizing: Coulter Sizing", Flow Cytometry and Sorting, 2. ed., pp 45-80, 1990 Wiley-Liss, Inc.).

The housing may further comprise one or more breather inlet/outlets communicating with the surroundings for preservation of substantially ambient atmospheric pressure in the housing flow system for facilitation of liquid flow in the housing flow system e.g. through the opening. One or more breakable seals may be provided for sealing one or more breather inlet/outlets during transport and storage. A breather inlet/outlet may connect a chamber and the surroundings for preservation of substantially ambient atmospheric pressure in the chamber.

Preferably, the housing constitutes a cartridge that is designed to be disposable after a single use. It is desirable that after use there is no need to clean the apparatus before it can be used in a new assay procedure with a new cartridge. Accordingly, escape of liquid from the cartridge at its entry into the docking station should be avoided. Preferably, a volume of liquid sufficient for the desired particle characterization can be drawn or pumped through the opening without the liquid passing out of the housing. Generally, it should be possible to pass a total volume of liquid, which is at least 0.1 ml to 10 ml, e.g. 1.5 ml, through the opening whilst particle characterization measurements are being made with no liquid leaving the housing.

The housing may comprise volume-metering means for determining the beginning and end of one or more, e.g. two or three, periods during which a predetermined volume of liquid has passed through the opening. Preferably, the one or more periods comprise a period for counting platelets and RBCs and a period for counting and differentiating between WBCs.

Preferably, the volume-metering means comprises a first volume-metering chamber with an input, e.g. communicating with the collection chamber, and an output, and wherein presence of liquid is detected at the input and at the output, respectively.

Further, the volume-metering means may comprise a second volume-metering chamber with an input communicating with the output from the first volume-metering chamber and an output, and wherein presence of liquid is detected at the input and at the output, respectively.

Preferably, the volume-metering means comprise one or more detection means. Preferably, the one or more detection means are positioned for facilitating sensing or determining, when liquid in the metering means is at or above respective levels in the volume-metering means, for example when a volume-metering chamber is filled with liquid. Preferably, the inputs and outputs of respective volume-metering chamber or chambers are provided with detection means.

The detection means may be optical detection means or optical detection parts, i.e. presence of liquid may be detected optically due to changed optical properties of an optical detection part, e.g. a channel configuration, from being filled with air till when it is being filled with liquid. This could be constructed as reflectance or transmittance detection from the surface, where incident light is reflected from an empty channel and transmitted through a filled channel, thus giving a clear shift in the detected reflected or transmitted light. Alternatively or in combination with the optical detection means, the detection means may comprise electrical sensors.

It is preferred that the inputs and the outputs of the metering chambers are formed by narrow channels for accommodation of only a small liquid volume compared to the volume of the metering chambers so that the actual positioning of the detection means, e.g. optical reflectance detection, in the channels do not substantially influence the accuracy of the volume metering determination.

The mixing chamber and/or the collection chamber may constitute one of the volume-metering chambers; however, it is preferred to provide independent volume-metering chambers facilitating positioning of the detection means, e.g. detection means for optical reflectance detection.

The volume-metering means may be used for sensing when the level of the liquid is such that a respective metering chamber or chambers are empty, filled, partly filled or not filled with liquid and may therefore serve for determining the beginning and/or end of one, two, three, or more periods during which a fixed volume of liquid has passed through the opening. For example, a first period of particle characterization, e.g. counting of platelets and RBCs, may begin when the level of the liquid just reaches or rises over the level of a first detection means and may end when the level of the liquid just reaches or rises over a second detection means, the volume of liquid passing through the opening during this period being defined by the volume of the space between the respective detection means. Further a third and/or a fourth detection means may be provided for determining the beginning and/or end of a second period of particle characterization, e.g. counting and differentiation of WBCs.

The housing may further comprise an overflow chamber for accommodation of liquid after passage through the opening.

A mixing member may be positioned in the mixing chamber. The mixing member may be a magnetic mixing member.

A part of the housing, e.g. the mixing chamber, may be adapted for spectrophotometric characterization, e.g. determination of haemoglobin in a liquid sample. The mixing chamber or other parts of the housing may comprise one or more windows to facilitate the spectrophotometric characterization.

The housing may further comprise a pump chamber communicating with the collection chamber and may have a pump actuator for causing a liquid flow through the opening. The pump actuator may be a piston or a membrane.

The docking station may comprise a pump device comprising one or more pumps and one or more directional valves for application of a pressure on the first port of the docking station and the second port of the docking station. Further, the docking station may comprise one or more engagement members for engagement with the first sampling member and/or the second sampling member when the cartridge is removably inserted into the docking station. The pump device and the one or more engagement members may be controlled according to a desired measuring cycle.

The docking station may further comprise one or more detectors and/or sensors, e.g. one or more optical detectors, for detecting presence of liquid in certain parts of the cartridge, e.g. in the detection means of the cartridge.

Thus, the apparatus according to the invention provides dual sample analysis by the Coulter Principle through one opening, facilitating determination of content of platelets, RBCs and WBCs in blood.

In accordance with a further aspect of the invention a method for characterizing particles in liquid is provided, the method comprising the steps of:
a) entering a first and a second liquid sample containing particles into a first and second cavity, respectively,
b) moving a first liquid through the first cavity and into a mixing chamber together with the first liquid sample,
c) performing first particle characterizing measurements by passage of at least a part of the first liquid sample from the mixing chamber through an opening and into a collection chamber,
d) moving a second liquid through the second cavity and into the mixing chamber together with the second liquid sample, and
e) performing second particle characterizing measurements by passage of at least a part of the second liquid from the mixing chamber through the opening and into the collection chamber.

Preferably, the method for characterizing particles in liquid is performed with an apparatus according to the description above.

The method is particularly intended for analysis of blood.

Preferably, step c) of performing first particle characterizing measurements comprises the step of counting of RBCs and platelets by Coulter Counting in at least a part of the first liquid sample.

Preferably, step e) of performing second particle characterizing measurements comprises the step of counting and differentiation of one or more different WBCs in at least a part of the second liquid sample.

Particle characterization performed in steps c) and/or e) may be started and/or stopped when a prescribed volume of liquid has passed through the opening.

Preferably, step b) and/or step d) comprise moving a mixing member in the mixing chamber for enhanced mixing of samples and liquid, and step b) may further comprise the step of priming and/or calibrating the apparatus with a part of the liquid in the mixing chamber.

The mixing ratio between the first liquid sample and liquid, e.g. substantially first liquid, in the mixing chamber just before first particle characterization measurements are performed may be in the range from about 1:2,000 to about 1:10,000, preferably about 1:10,000, and the mixing ratio between the second liquid sample and liquid, e.g. substantially a mixture of first and second liquids, in the mixing chamber just before second particle characterization measurements are performed may be in the range from about 1:100 to about 1:2,000, preferably about 1:500.

Preferably, the first liquid is a conductive liquid facilitating Coulter analysis of the first and second liquid samples.

Preferably, the second liquid is a lysing agent for lysing of RBCs in the mixing chamber facilitating counting and determination of different WBCs in the second liquid sample.

Additionally, the content of haemoglobin may be determined by spectrophotometric characterization. Preferably, spectrophotometric characterization is performed through a window in the mixing chamber between step d) and step e).

According to the present invention, a device for sampling a small and accurate volume of liquid is provided, comprising a housing comprising a first connecting part and a second connecting part, and a first sampling member that is movably positioned in the housing and having a recess in its surface, the recess and an abutting surface of the housing defining a cavity for receiving and holding a liquid sample. In a first position of the first sampling member, the cavity is in communication with the first connecting part and the second connecting part, the first connecting part functioning as an inlet for the liquid sample and the second connecting part functioning as an outlet for the liquid sample, and, in a second position, the cavity is enclosed within the housing and the sampling member.

The first connecting part may form a first capillary tunnel and be adapted so that, upon contact between the first connecting part and liquid to be sampled, a sample of the liquid is drawn into the first connecting part by capillary attraction.

The cavity may form a capillary tunnel that is adapted for drawing the liquid sample into the cavity by capillary attraction.

The sampling member may be rotatable about an axis of rotation that is substantially perpendicular to a longitudinal axis of the cavity.

The sampling member may be displaced in a direction substantially perpendicular to a longitudinal axis of the cavity.

The housing may further comprise a liquid storage chamber such that the liquid sample in a second position of the cavity is in communication with a liquid in the liquid storage chamber.

BRIEF DESCRIPTION OF THE DRAWINGS

The invention will now be further described and illustrated in further detail with reference to the accompanying drawings in which.

DETAILED DESCRIPTION

The same reference number denotes corresponding elements in the different embodiments in the figures.

Figure 1:
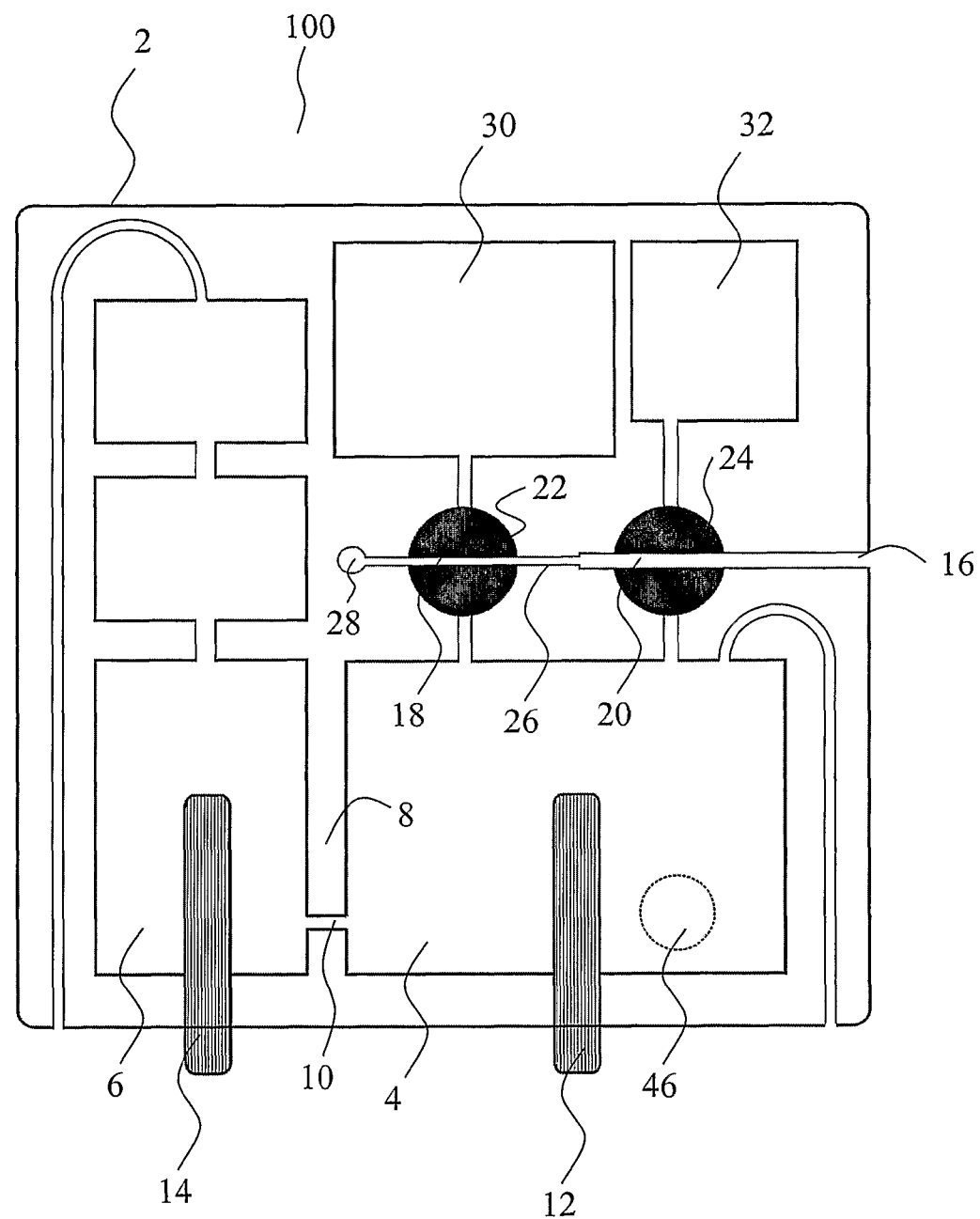
FIG. 1 schematically shows one embodiment of an apparatus according to the invention, FIG. 2 schematically shows the embodiment of FIG. 1 with first and second cavities in their second positions, FIG. 3 schematically shows another embodiment of an apparatus according to the invention, FIG. 4 schematically shows another embodiment of an apparatus according to the invention.

FIG. 1 schematically shows one embodiment of the apparatus according to the invention. The figure shows a disposable cartridge 100 for Complete Blood Counts (CBC), i.e. counting of red blood cells (RBCs), blood platelets (PLTs), white blood cells (WBCs) including a differential count of subpopulations of WBCs. Furthermore, the cartridge includes means for determination of other blood constituents such as haemoglobin, blood gasses (such as pH) or proteins (such as C-reactive protein) or the like.

The cartridge 100 comprises a housing 2 with a mixing chamber 4 and a collection chamber 6 separated by a wall 8 containing an opening 10 for the passage of particles in liquid between the mixing chamber and the collection chamber. Particle characterization means 12, 14 are provided for characterizing particles passing through the opening 10.

The housing further comprises a first bore 16 in the outer surface of the housing for entrance of liquid and a first cavity 18 for receiving and holding a first liquid sample. In a first position as shown in the figure, the first cavity 18 is positioned for entrance of the first liquid sample into the first cavity. The first cavity 18 is movably positioned in relation to the housing 2 in such a way that, in a second position, the first cavity is in communication with the mixing chamber 4 for discharge of the first liquid sample into the mixing chamber 4. Further, a second cavity 20 for receiving and holding a second liquid sample is provided. The second cavity 20 is movably positioned in relation to the housing 2 in such a way that, in a first position, the second cavity is in communication with the first bore 16 for entrance of the second liquid sample into the second cavity 20. In a second position, the second cavity 20 is in communication with the mixing chamber 4 for discharge of the second liquid sample into the mixing chamber 4.

In this embodiment, the first cavity 18 extends as a channel through a first sampling member 22 that can be rotated around an axis perpendicular to the figure, and the second cavity 20 extends as a channel through a second sampling member 24 that can be rotated around an axis perpendicular to the figure. The respective channels in the respective sampling members form the first cavity 18 and the second cavity 20.

In the first position of the first cavity, the first cavity 18 is in communication with a connecting channel 26 extending from the first sampling member to the second sampling member, and in the first position of the second cavity, the second cavity 20 is in communication with the first bore 16 and the connecting channel 26. When in their respective first positions as seen in FIG. 1, the first cavity 18 and the second cavity 20 form a capillary with the first bore 16 and the connecting channel 26. The first cavity is in communication with an outlet 28 that allows air to escape out of the capillary and out of the housing allowing sample entry. By turning the first and second sampling members 22, 24, precise volumes of liquid, such as blood, are trapped inside the cavities 18, 20.

Preferably, the volumes of the first cavity and the second cavity are different. The volume of the first cavity and thus substantially the volume of the first sample may range from 0 to 10 µL, such as from 0.1 to 1 µL, preferably 0.2 µL. The volume of the second cavity and thus substantially the volume of the second sample may range from 0 to 100 µL, such as from 0.5 to 10 µL, preferably 2 µL.

Figure 2:
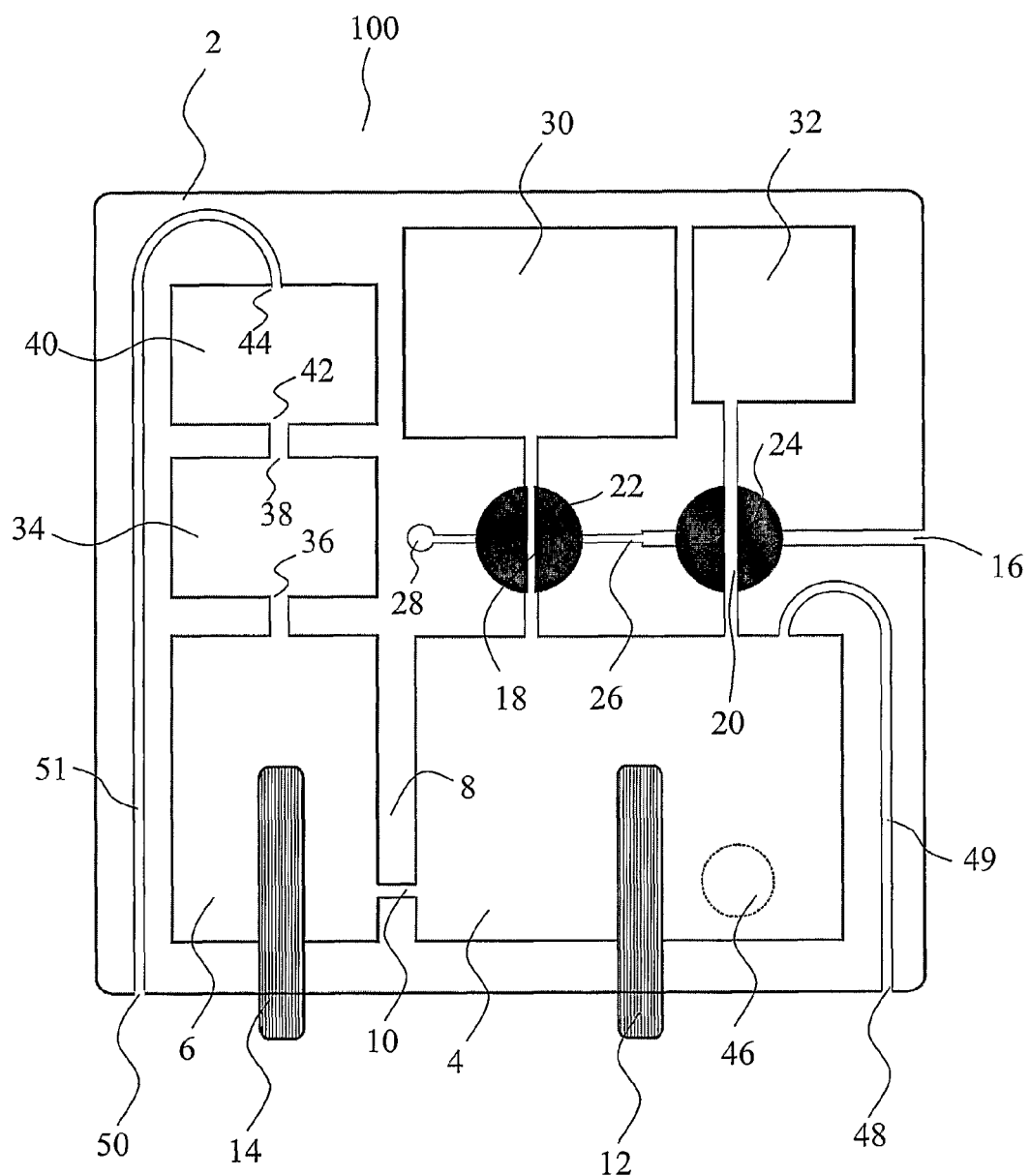

FIG. 2 shows the embodiment of FIG. 1 with the first cavity 18 and the second cavity 20 in their respective second positions.

In the second position of the first cavity, the first cavity 18 is in communication with the mixing chamber 4. Further, the first cavity 18 is in communication with a first liquid storage chamber 30 through a short duct. Preferably, first liquid in the first liquid storage chamber 30 is pumped through the first cavity, thereby filling or flushing the first liquid sample and the first liquid into the mixing chamber 4 thus forming a precisely diluted and analytically prepared blood sample.

In the second position of the second cavity, the second cavity 20 is in communication with the mixing chamber 4.

Further, the second cavity 20 is in communication with a second liquid storage chamber 32 through a short duct. Preferably, second liquid in the second liquid storage chamber 32 is pumped through the second cavity, thereby filling or flushing the second liquid sample and the second liquid into the mixing chamber 4 thus forming a precisely diluted and analytically prepared blood sample.

Blood samples partly or fully constituting first and second liquid samples in the first cavity and the second cavity, respectively, may thus be diluted and prepared for analysis in the mixing chamber 4. The samples are analyzed by impedance sizing, i.e. the Coulter Principle, through the orifice 10 in the wall 8 of the mixing chamber. A conductive liquid forms an electrical connection from the first electrode 12 in the mixing chamber 4 to the second electrode 14 in the collection chamber 6. Changes in impedance of the electrical connection originating from cells passing in a liquid flow through the orifice 10 can be recorded for counting and sizing of the cells.

Further, the cartridge comprises a first volume-metering chamber 34 with an input 36 communicating with the collection chamber and an output 38, and wherein presence of liquid is detected at the input and at the output, respectively.

Furthermore, the cartridge comprises a second volume-metering chamber 40 with an input 42 communicating with the output 38 from the first volume-metering chamber 34 and an output 44, and wherein presence of liquid is detected at the input and at the output, respectively.

The respective inputs and outputs of the metering chambers are formed by narrow channels for accommodation of only a small liquid volume compared to the volume of the metering chambers. The narrow channels are a part of the detection means, as the narrow channels are employed for optical reflectance detection.

The volume-metering chambers 34, 40 can be used to determine and control volume for calculating the concentrations of the counted cells and thus define periods of measurement.

The housing 2 further comprises a first port 48 communicating with the mixing chamber for causing a liquid flow from the liquid storage chambers 30, 32 through the first cavity 18 and the second cavity 20, respectively. A pressure applied to the first port may cause a liquid flow through the first cavity 18 and/or the second cavity 20 into the mixing chamber.

A first channel 49 connects the mixing chamber and the first port 48.

The housing 2 further comprises a second port 50 communicating with the collection chamber for causing a liquid flow through the opening 10. The second port 50 is in communication with the collection chamber via the volume-metering chambers 34, 40. A pressure applied to the second port may cause a liquid flow through the opening 10.

A second channel 51 connects the second port 50 and the second volume-metering chamber 40.

Spectrophotometric measurements can be established through a small window 46 in the mixing chamber 4.

A method of performing particle characterization according to the invention is now illustrated by an example of performing CBC in the cartridge in FIG. 1 and 2. The method for CBC comprises the following steps:
  blood is drawn by capillary forces into the first bore 16 filling the first cavity 18 and the second cavity 20 in their first positions,
  the first cavity 18 is moved to its second position by turning the first sample member 22,
  the first blood sample in the first cavity 18 is diluted a factor 1:10,000 with an isotonic diluent from the first liquid storage chamber 30, by pumping first liquid from the first liquid storage chamber 30 through the first cavity 18 and into the mixing chamber 4,
  RBCs and PLTs are counted in a first period for particle characterization during filling of the first volume-metering chamber 34 by a liquid flow from the mixing chamber 4 through the opening 10 to the collection chamber 6 and subsequently to the first volume-metering chamber 34,
  the flow through the opening 10 is stopped,
  the second cavity 20 is moved to its second position by turning the second sample member 24,
  the remaining liquid in the mixing chamber 4 is mixed with the second blood sample from the second cavity 20 and the second liquid in the second liquid storage chamber 32 to obtain a substantially 1:500 dilution of the second blood sample, by pumping second liquid from the second liquid storage chamber 32 through the second cavity 20 and into the mixing chamber 4,
  the second liquid lyses the RBCs in the remaining first blood sample (negligible) and the second blood sample and transforms the haemoglobin into a measurable and stable component. The concentration of haemoglobin is measured through the window 46 in the mixing chamber 4 by absorption,
  WBCs are counted in a second period for particle characterization during filling of the second volume-metering chamber 40. Counting of WBCs include identification of the WBC subtypes (three or five part differentials), e.g. lymphocytes, monocytes and granulocytes.

In one embodiment, first liquid is pumped from the first liquid storage chamber 30 through the first cavity 18 and into the mixing chamber 4 by applying a first pressure to the collection chamber 4 via the first channel 49, wherein the first pressure is higher than the pressure in the first liquid storage chamber 30. Due to the difference in pressure between the first liquid storage chamber 30 and the mixing chamber 4, air bubbles move through the first cavity to substantially equalize the pressure in the first liquid storage chamber 30 and the mixing chamber 4. Subsequently, a second pressure is applied to the mixing chamber 4, wherein the second pressure is lower than the pressure in the first liquid storage chamber 30. Due to the difference in pressure between the first liquid storage chamber 30 and the mixing chamber 4, and orientation of the cartridge, at least a part of the first liquid and the first liquid sample moves through the first cavity into the collection chamber to substantially equalize the pressure in the first liquid storage chamber 30 and the mixing chamber 4. This operation may be repeated until the first liquid storage chamber 30 is substantially empty. The first pressure and the second pressure may also be applied to the collection chamber 6 to substantially avoid liquid transport between the mixing chamber 4 and the collection chamber 6 in this step. The first pressure and/or the second pressure may be applied via the second channel 51.

Likewise, second liquid is pumped from the second liquid storage chamber 32 through the second cavity 20 and into the mixing chamber 4 by applying alternating pressures to the mixing chamber 4.

Figure 3:
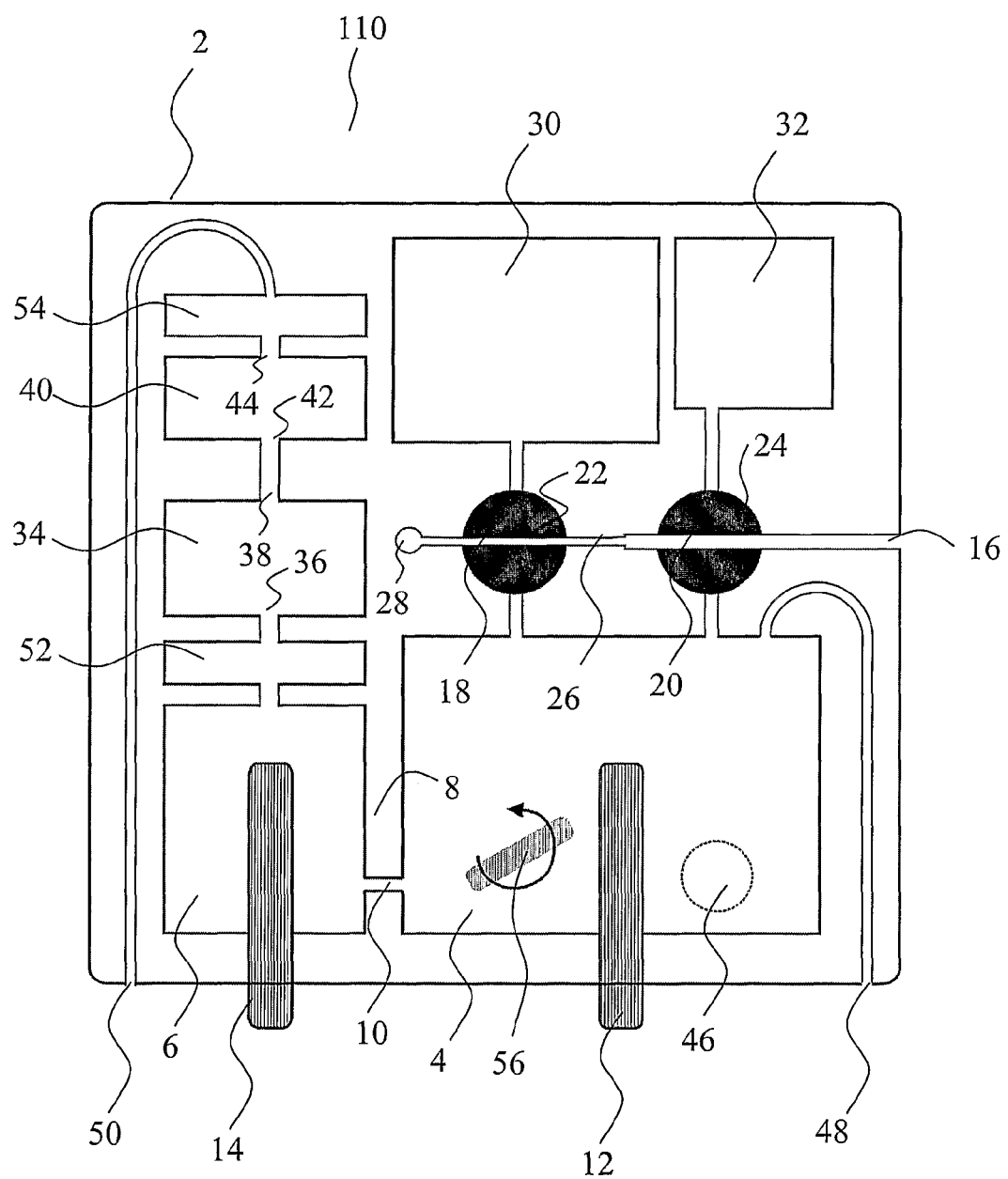

FIG. 3 shows another embodiment of the present invention. The cartridge 110 comprises a third volume-metering chamber 52 between the collection chamber 6 and the first volume-metering chamber 34. Presence of liquid is detected at the input and at the output, respectively. The third volume-metering chamber 52 may be employed to control a third period for calibration before first and second particle characterization. Further, the housing 2 comprises an overflow chamber 54 in order to prevent liquid from flowing out through second port 50. Other embodiments, e.g. embodiments schematically illustrated in FIGS. 1-2 and FIGS. 4-14, may also comprise a third volume-metering chamber between the collection chamber 6 and the first volume-metering chamber 34 and/or an overflow chamber.

Additionally, the mixing chamber 4 may have a small magnetic mixing member 56 included for forced mixing of liquid by stirring. The mixing member is rotated by an externally rotating magnetic field that is strong enough to hold the mixing member oriented according to the magnetic field. Other embodiments, e.g. the embodiments illustrated in FIGS. 1-2 and FIGS. 4-14, may comprise a mixing member.

The presence of liquid in the channels constituting the inputs and outputs of the volume-metering chambers 34, 40, 52 can be detected by optical detection means. The refractive index of the interface between the housing and the channel will vary as the channel is filled with liquid instead of air. The incident light from a light source (not shown) will be reflected with an empty channel, and a sensor (not shown) records the reflected light. When the channel is filled with liquid the light is no longer reflected and the sensor records the change.

Figure 4:
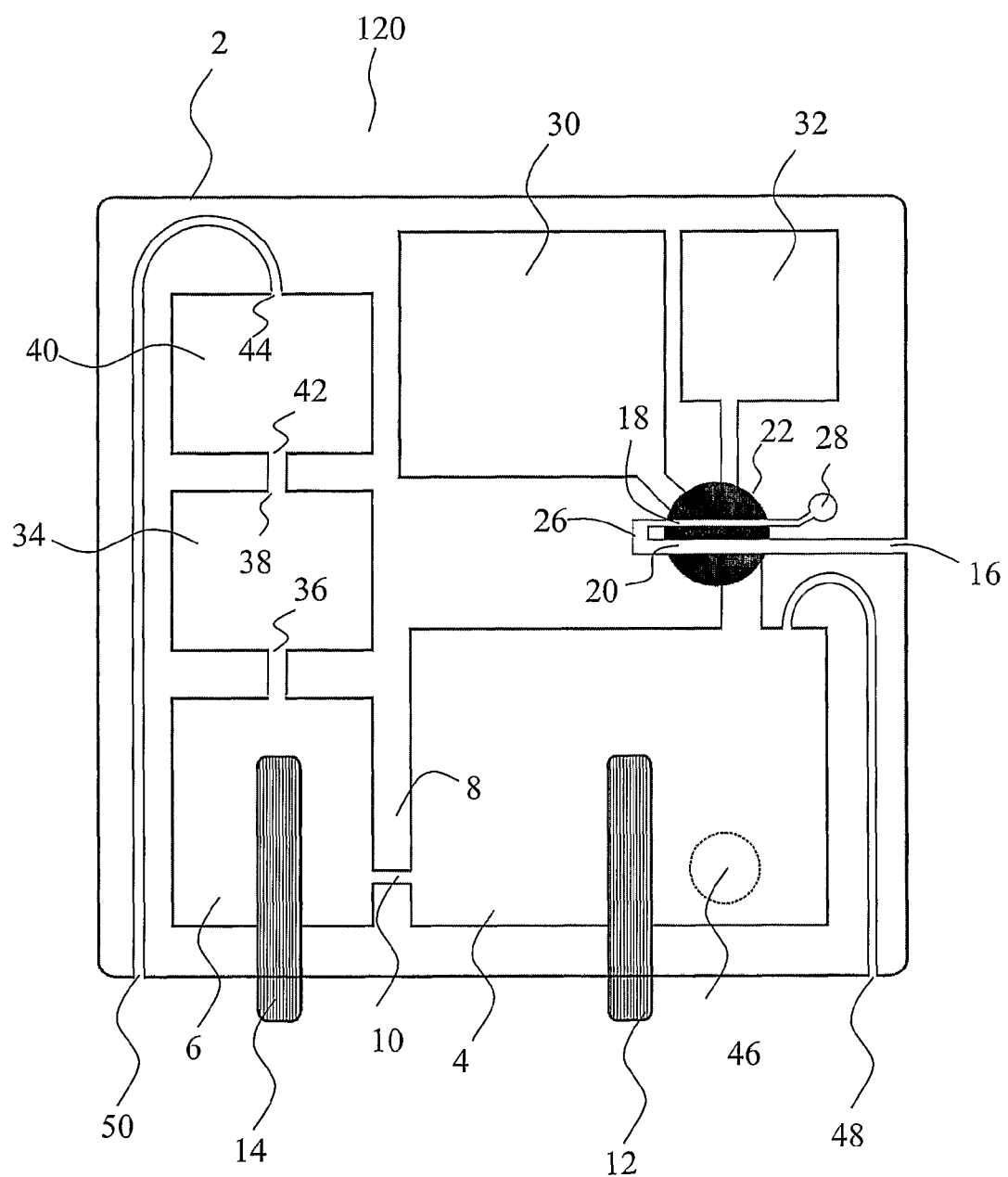

FIG. 4 shows another embodiment of the present invention. The cartridge 120 comprises a first sampling member 22 comprising the first cavity 18 and the second cavity 20. The first sampling member is in a first position and thus first and second cavities are in their first positions for filling blood into the cavities by capillary forces as described above.

Figure 5:
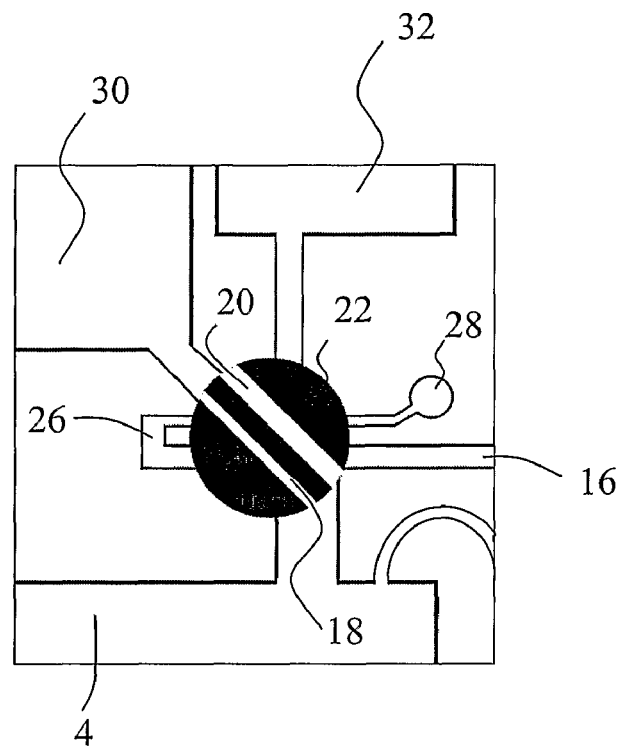
FIG. 5 shows a section of the embodiment in FIG. 4 with the first cavity in a second position.

FIG. 5 shows a section of the cartridge 120 with the first sampling member 22 in a second position. The first cavity 18 is in its second position and in communication with the mixing chamber 4. Further, the first cavity 18 is in communication with a first liquid storage chamber 30 through a short duct, thereby connecting the first liquid storage chamber 30 and the mixing chamber 4. The second cavity 20 is not in communication with the first liquid storage chamber 30

Figure 6:
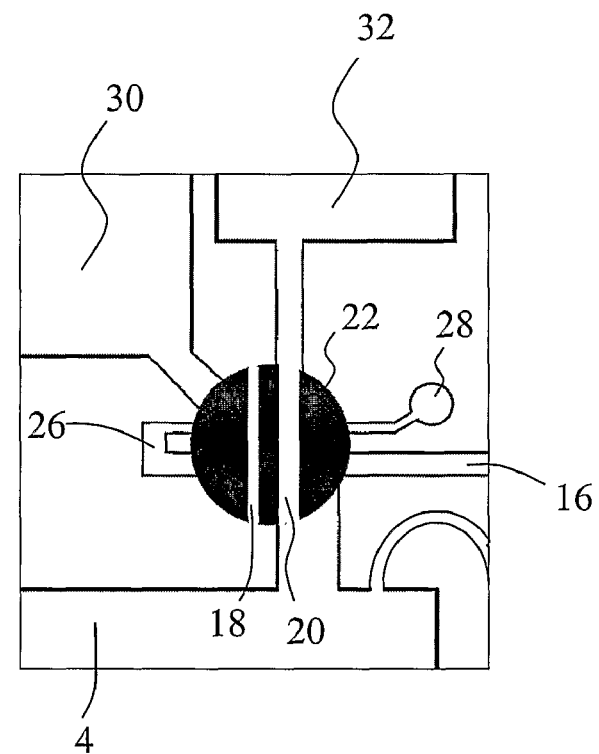
FIG. 6 shows a section of the embodiment in FIG. 4 with the second cavity in a second position, FIG. 7 schematically shows yet another embodiment of an apparatus according to the invention, FIG. 8 schematically shows still another embodiment of an apparatus according to the invention.

FIG. 6 shows a section of the cartridge 120 with the first sampling member 22 in a third position. The second cavity 20 is in its second position and in communication with the mixing chamber 4. Further, the second cavity 20 is in communication with a second liquid storage chamber 32 through a short duct thereby connecting the second liquid storage chamber 32 and the mixing chamber 4.

Figure 7:
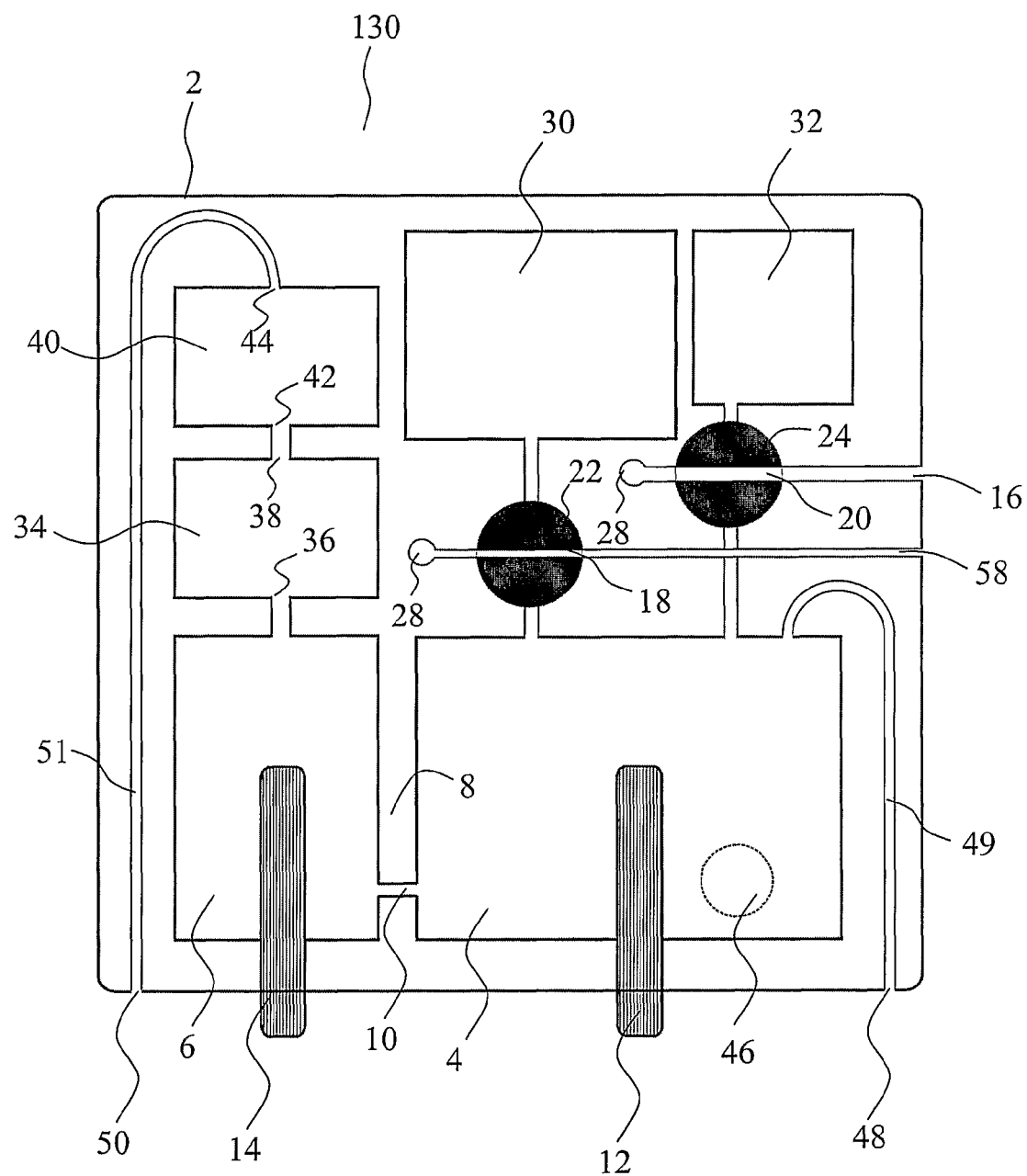

FIG. 7 shows another embodiment of the present invention, where the first cavity 18 is in its first position and communicates with a second bore 58 for entrance of liquid to be sampled.

Figure 8:
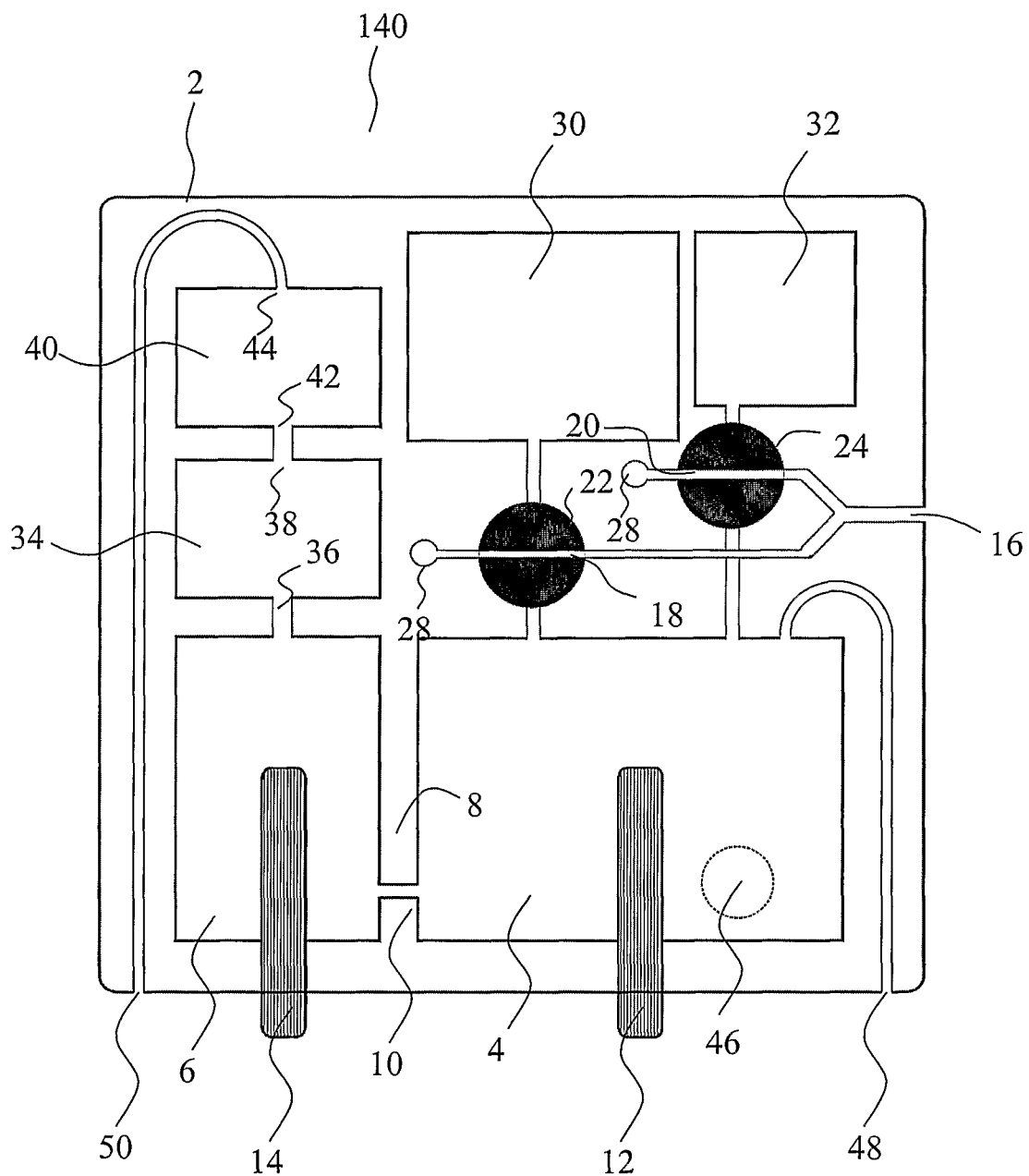

FIG. 8 shows another embodiment of the present invention. In their first positions, the first cavity 18 and the second cavity 20 are in parallel communication with the first bore 16 for entrance of liquid into the first cavity and the second cavity.

Figure 9:
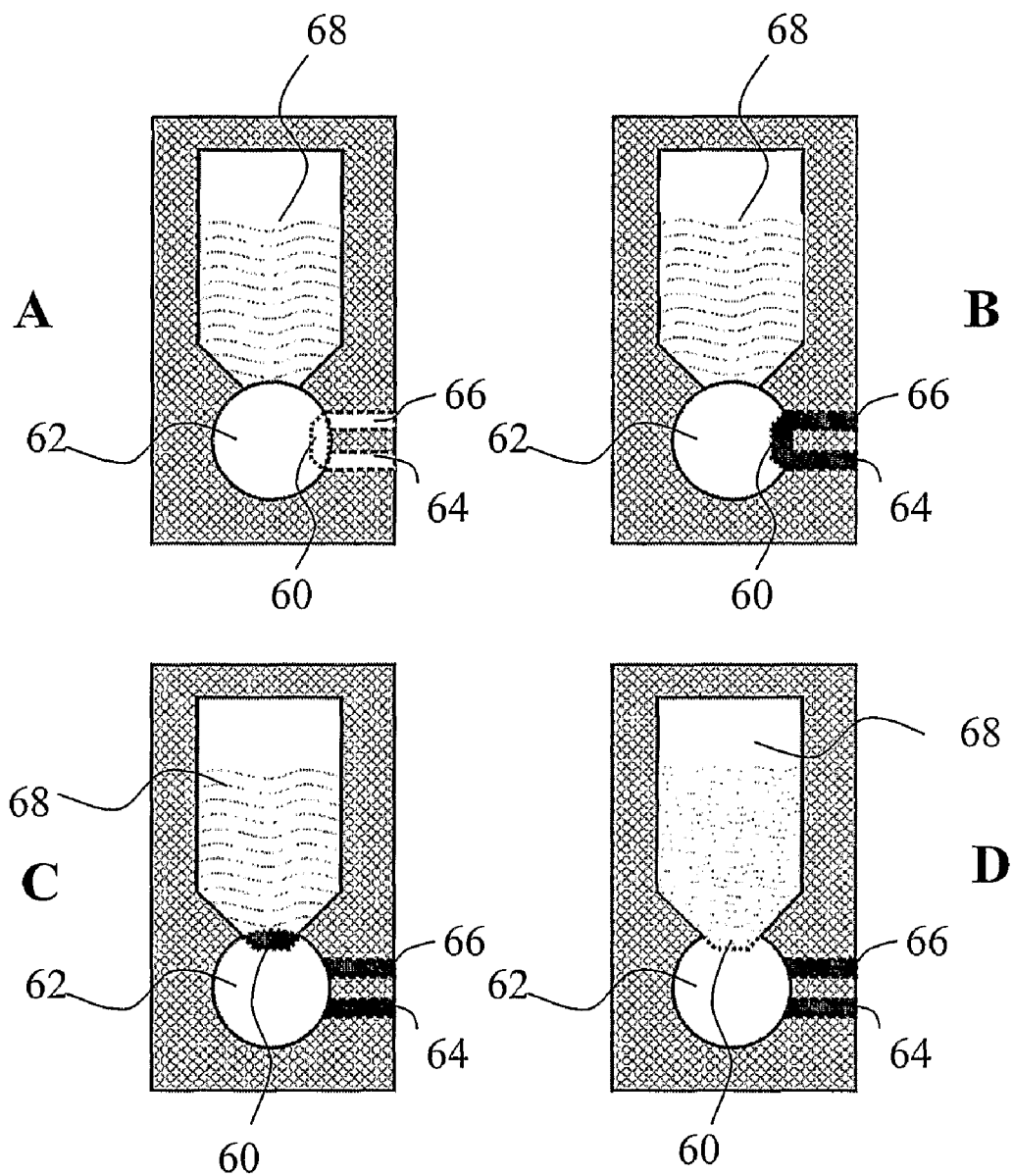
FIG. 9 shows a new sampling principle for sampling very small amounts of liquid, FIG. 10 schematically shows yet another embodiment of an apparatus according to the invention.

FIG. 9 shows a new sampling principle for sampling a very small amount of blood, such as from 0 to 1 μL, e.g. from 0 to 0.5 μL, from about 0.1 μL to about 0.3 μL, preferably 0.2 μL. A device for sampling a small an accurate volume of liquid comprises a housing and a sampling member having a recess in its surface thereby defining a cavity with an abutting surface of the housing. The small cavity 60 in the sampling member 62 is connected to connecting parts 64, 66, preferably capillaries, for filling of blood. Preferably, the cavity 60 is a recess in the surface of the sampling member and may contain a very small amount of blood and thus provide a high dilution rate with reagent in the liquid storage chamber 68. The small blood sample volume is difficult to make in a channel, because of the very small diameter required. A small cavity in the surface of the sampling member can be used for sampling very small amounts of blood with high reproducibility.

FIG. 9A shows the device with the cavity in the first position before filling of blood. FIG. 9B shows the capillaries 64, 66 and cavity 60 filled with blood. FIG. 9C shows the sampling member 62 turned into a second position for diluting the precise amount of blood in the cavity. The cavity is in communication with the liquid storage chamber 68. In FIG. 9D the blood has been diluted with reagent in the liquid storage chamber. Dilution of the blood may take place by stirring or by washing the cavity with the diluent.

Figure 10:
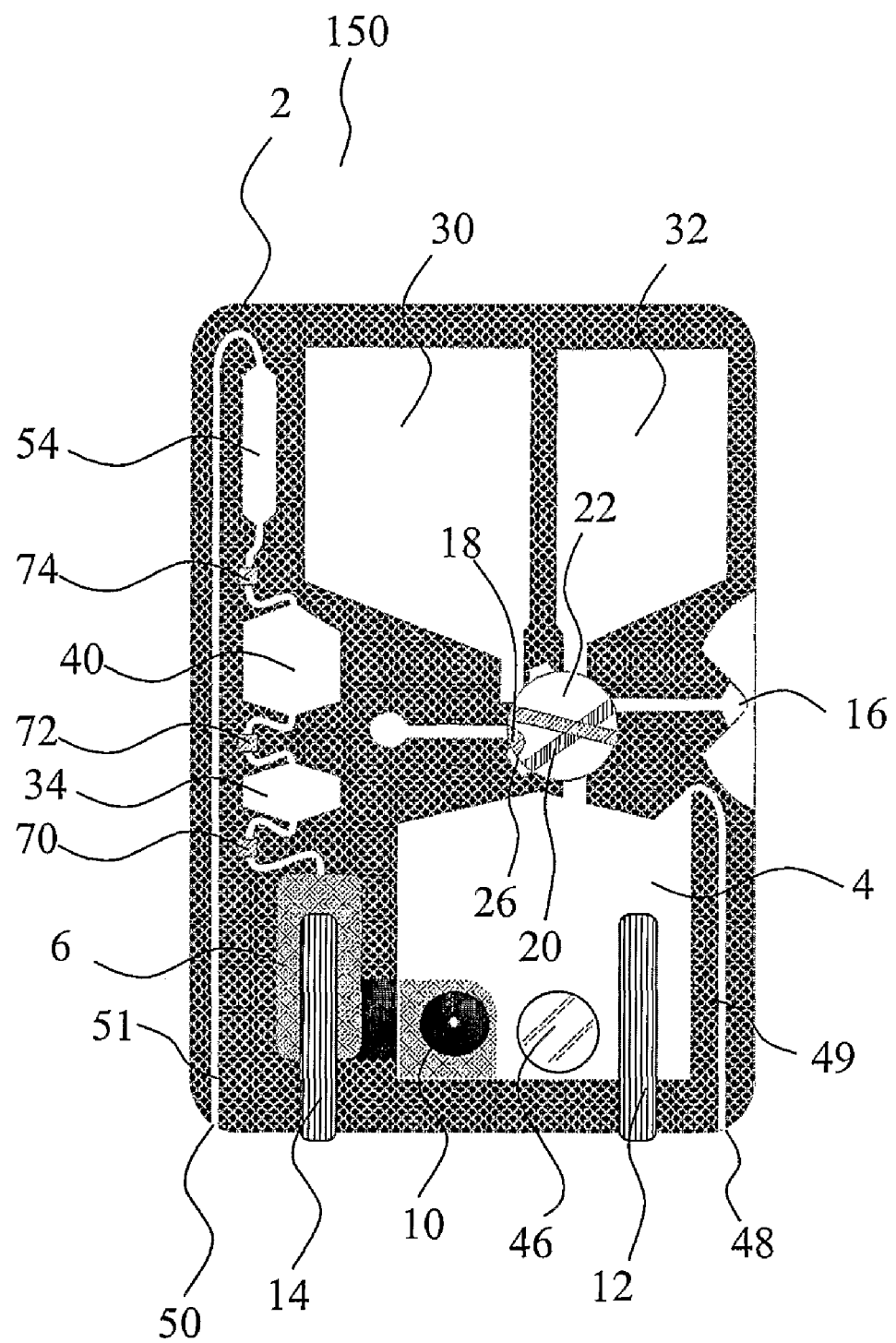

FIG. 10 shows an embodiment 150 of the present invention employing the new sampling principle for sampling a very small amount of blood as shown in FIG. 9A-D. The first cavity 18 is a recess on the surface of the first sampling member 22.

In the first position of the first cavity, the first cavity 18 is in communication with a connecting channel 26, and in the first position of the second cavity, the second cavity 20 is in communication with the first bore 16 and the connecting channel 26. The first cavity 18 and the second cavity 20 form a capillary with the first bore 16 and the connecting channel 26.

The collection chamber 6 extends behind the mixing chamber 4, such that a wall containing the opening 10 separates the mixing chamber 4 and the collection chamber 6 according to the same principle as schematically illustrated in FIGS. 1-3. Detection means 70, 72, 74 for detecting presence of liquid in channels at the inputs and outputs of the volume-metering chambers 34, 40 are provided for determining and/or controlling one, two or more periods of measurement. Priming and/or calibration of the apparatus may be performed during filling of the collection chamber, e.g. until the liquid level reaches detection means 70.

Figure 11:
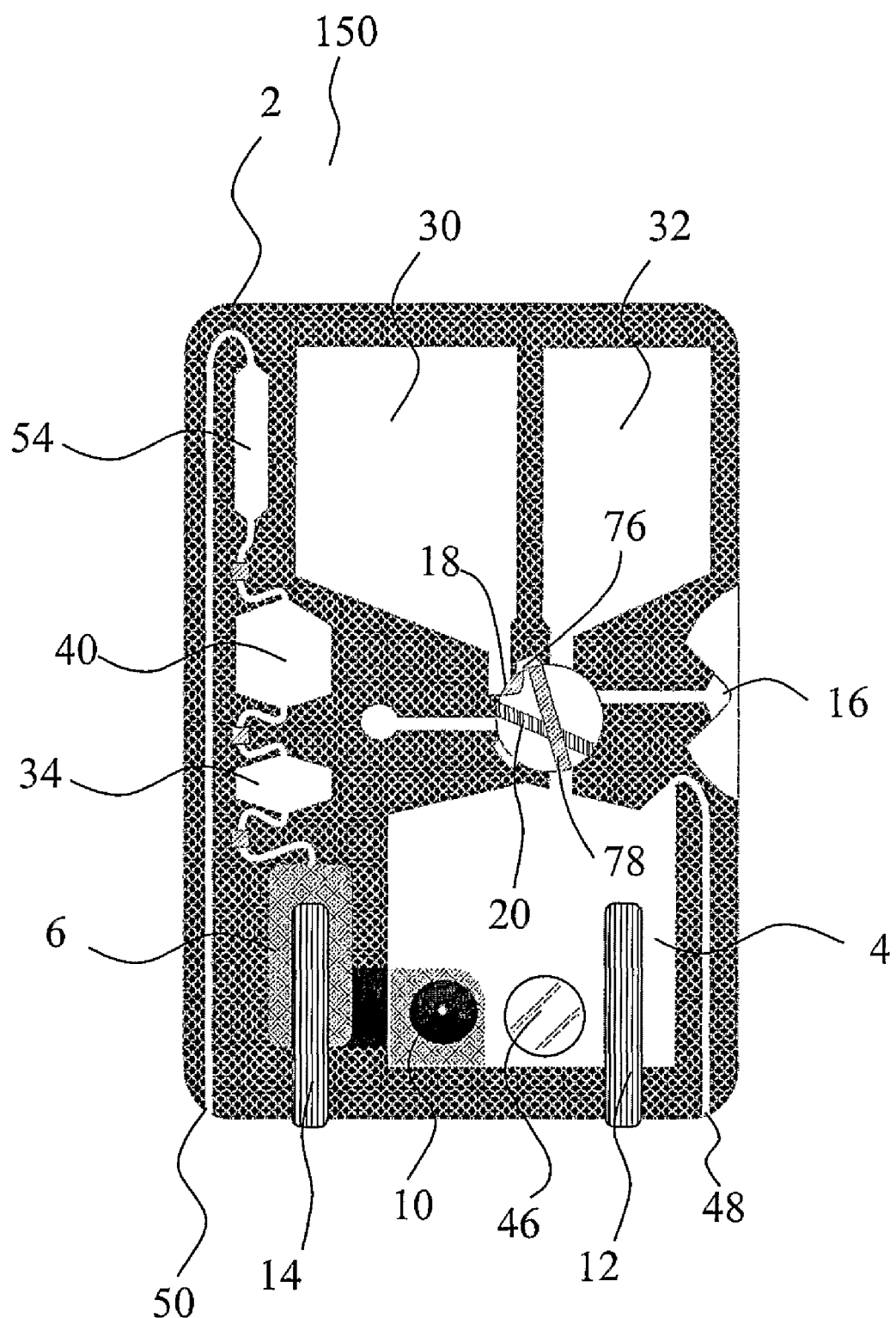
FIG. 11 shows the embodiment in FIG. 10 with the first cavity in a second position.

FIG. 11 shows the embodiment in FIG. 10 with the first cavity 18 in a second position. The first cavity is in communication with the mixing chamber 4 via a connecting part 76 and a channel 78 in the sampling member. The first liquid storage chamber 30 is also in communication with the first cavity such that first liquid in the first liquid storage chamber and the first liquid sample in the first cavity can be moved to the mixing chamber 4.

Figure 12:
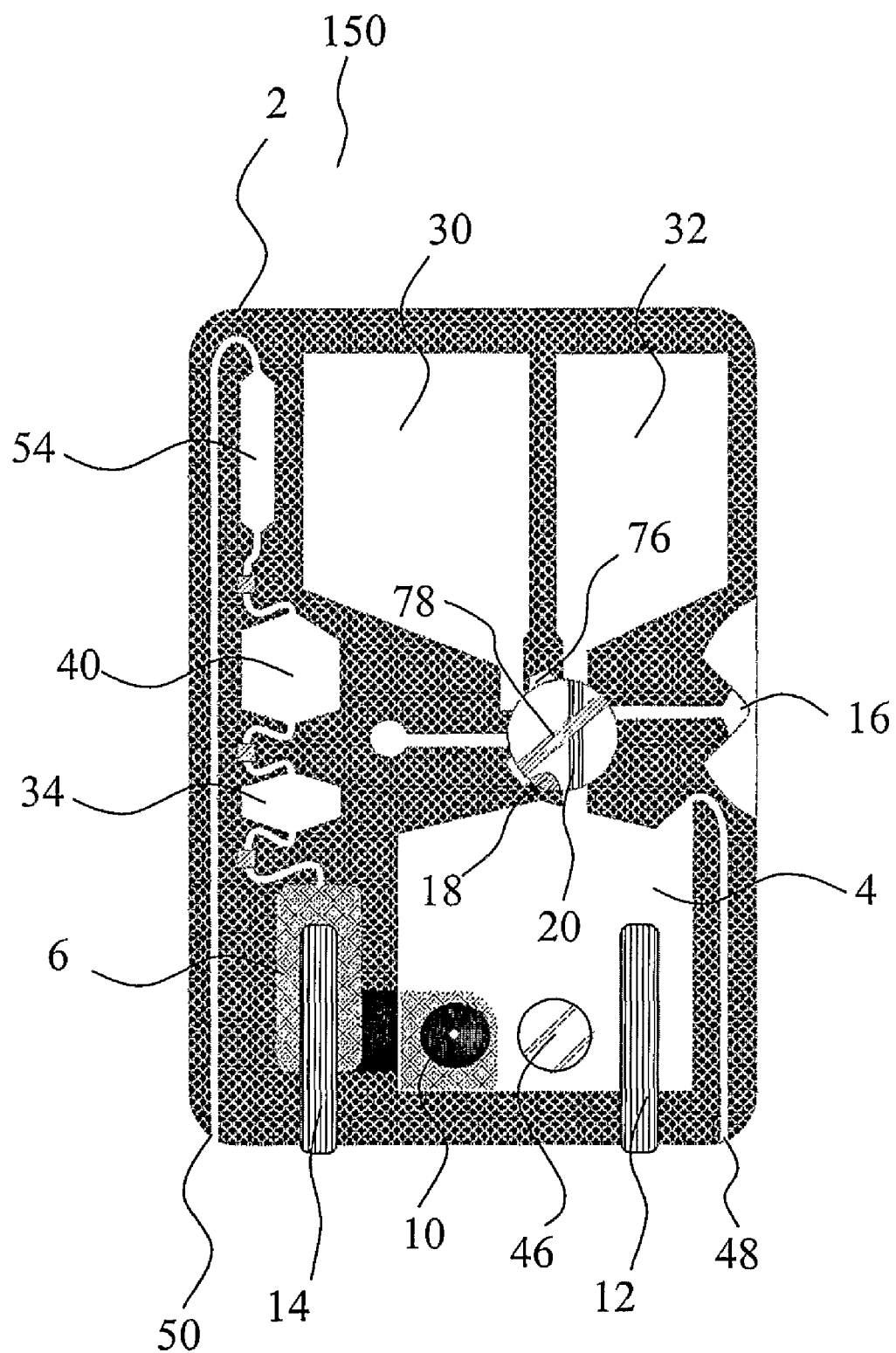
FIG. 12 shows the embodiment in FIG. 10 with the second cavity in a second position, FIG. 13 schematically shows still another embodiment of an apparatus according to the invention, FIG. 14 schematically shows an embodiment of an apparatus according to the invention.

FIG. 12 shows the embodiment in FIG. 10 with the second cavity 20 in a second position. The second cavity is in communication with the mixing chamber 4. The second liquid storage chamber 32 is also in communication with the second cavity such that second liquid in the second liquid storage chamber and the second liquid sample in the second cavity can be moved to the mixing chamber 4.

Figure 13:
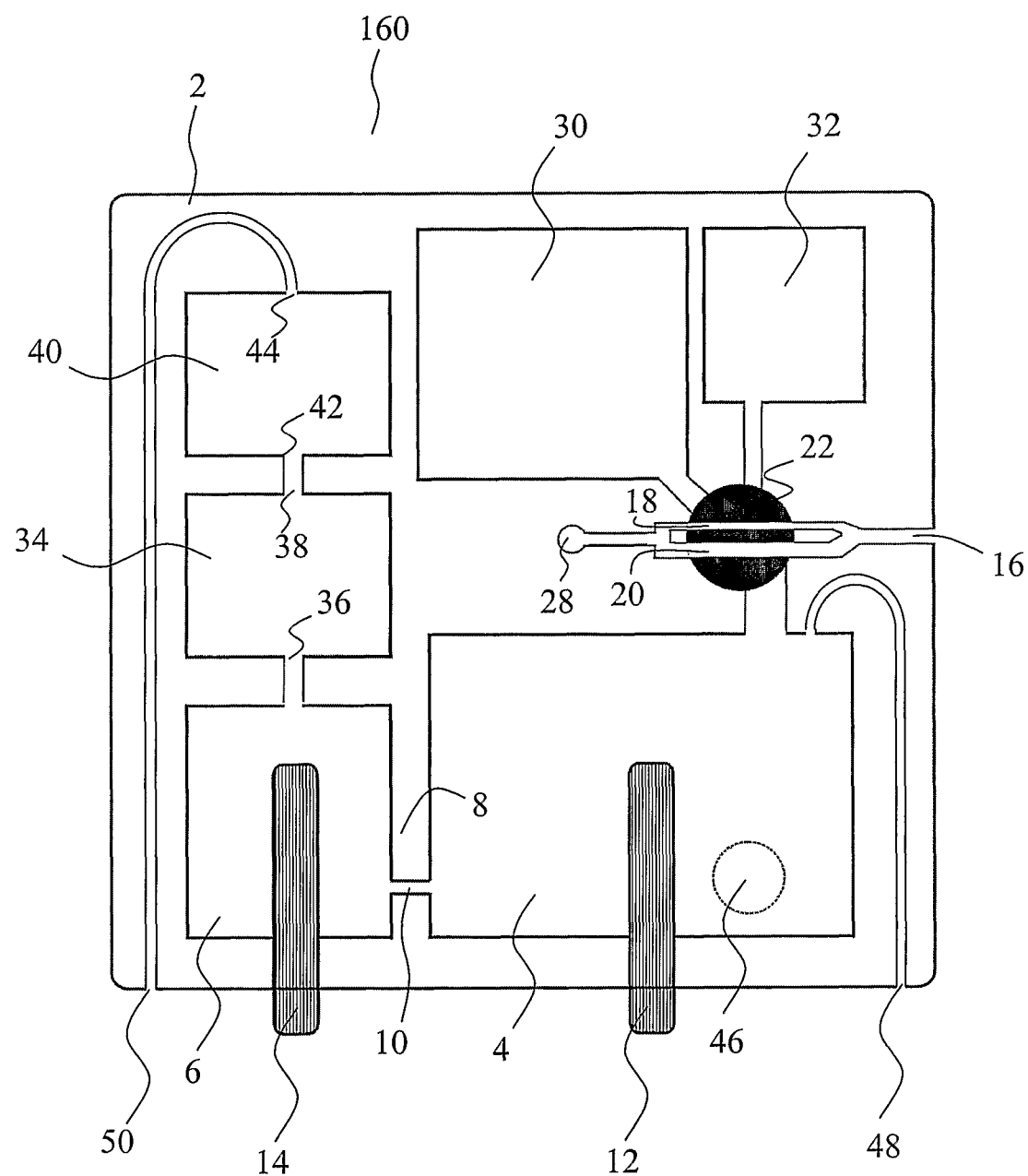

FIG. 13 shows another embodiment of the present invention, where the first cavity 18 and the second cavity 20 are comprised in the first sampling member 22 and connected in parallel with the first bore 16.

Figure 14:
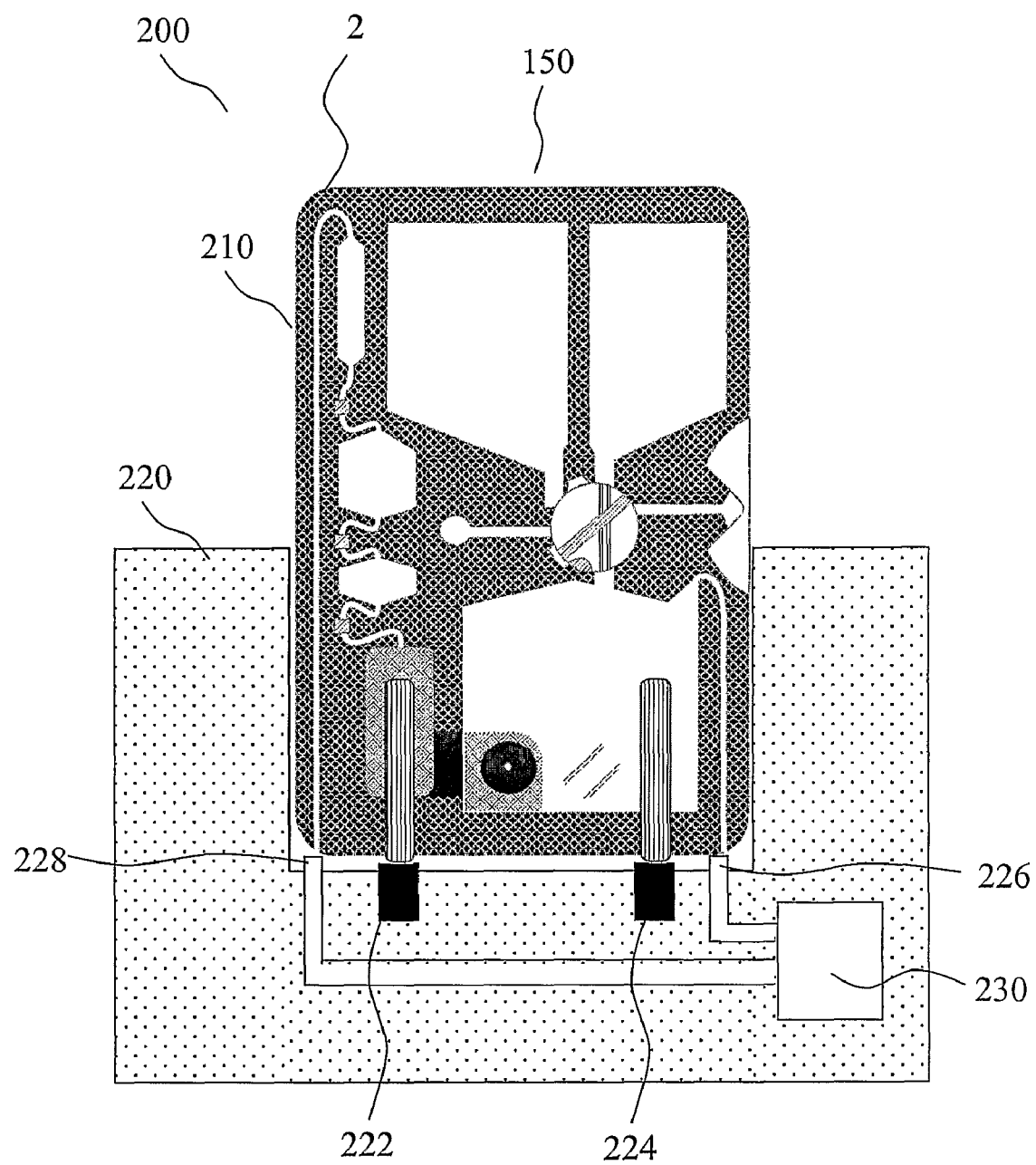

FIG. 14 illustrates one embodiment of an apparatus for characterizing particles suspended in a liquid. The apparatus comprises a housing 150 constituting a cartridge 210, and a docking station 220 for removably receiving the cartridge 210. It is to be understood that the docking station 220 may be adapted for receiving and/or operating other embodiments of a housing according to the present invention, e.g. the embodiments schematically illustrated in FIGS. 1-8 and FIG. 13. The docking station 220 comprises a first connector 222 and a second connector 224 for operational connection with the particle characterization means when the cartridge is received in the docking station. The docking station 220 comprises a first port 226 communicating with the first port in the cartridge 210 for forming a substantially tight gas connection between the first ports when the cartridge is inserted in the docking station. The substantially tight gas connection provides for application of a pressure causing a liquid flow through the first cavity and the second cavity.

The docking station 220 further comprises a second port 228 communicating with the second port in the cartridge 210 for forming a substantially tight gas connection between the second ports when the cartridge is inserted in the docking station. The substantially tight gas connection provides for application of a pressure causing a liquid flow through the opening.

The docking station 220 comprises a pump device 230 comprising one or more pumps and one or more directional valves for application of a pressure on the first port 226 and/or the second port 228. Further, the docking station may comprise one or more engagement members (not shown) for engagement with and moving the first sampling member and/or the second sampling member when the cartridge is removably inserted into the docking station. Operation of the pump device and the one or more engagement members is controlled according to a desired method of measuring.

Different features of the illustrated embodiments may be combined.

Figure 15:
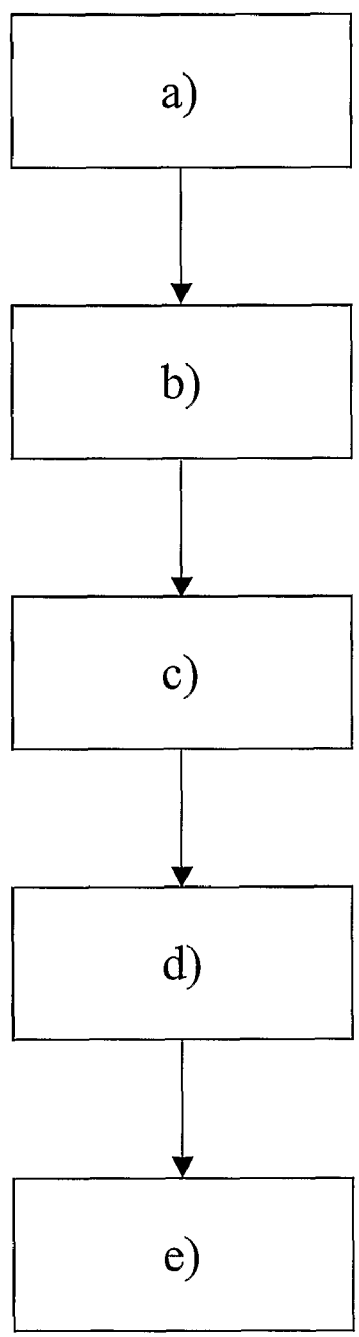
FIG. 15 illustrates one embodiment of the method according to the invention.

FIG. 15 illustrates a preferred embodiment of the method according to the invention. In the illustrated embodiment, step a) comprises entering a first and a second liquid sample containing particles into a first and second cavity, respectively. Step b) comprises moving a first liquid through the first cavity and into a mixing chamber together with the first liquid sample, and step c) comprises performing first particle characterizing measurements by passage of at least a part of the first liquid sample from the mixing chamber through an opening and into a collection chamber. Step d) comprises moving a second liquid through the second cavity and into the mixing chamber together with the second liquid sample, and step e) comprises performing second particle characterizing measurements by passage of at least a part of the second liquid from the mixing chamber through the opening and into the collection chamber. Preferably, steps b) and d) are performed as described in connection with FIGS. 1 and 2.

The invention claimed is:

1. An apparatus for characterizing particles in liquid, comprising a housing with
    a first mixing chamber and a first collection chamber separated by a wall containing an opening for passage of the particles between the first mixing chamber and the first collection chamber,
    particle characterization means for characterizing particles passing through the opening,
    a first bore in the outer surface of the housing for entrance of liquid samples,
    a first cavity for receiving and holding a first liquid sample, the first cavity being movably positioned in relation to the housing, and
    a second cavity for receiving and holding a second liquid sample, the second cavity being movably positioned in relation to the housing in such a way that, in a first position, the second cavity is in communication with the first bore for entrance of the second liquid sample into the second cavity, and, in a second position, the second cavity is in communication with the first mixing chamber for discharge of the second liquid sample into the first mixing chamber,
    wherein the first cavity in a first position is in communication with the first bore in the outer surface of the housing for entrance of the first liquid sample into the first cavity, and, in a second position, the first cavity is in communication with the first mixing chamber for discharge of the first liquid sample into the first mixing chamber.

2. An apparatus according to claim 1, wherein in the first positions, the first cavity, the second cavity and the first bore are connected in series for entrance of the first and second liquid samples into the first cavity and the second cavity, respectively.

3. An apparatus according to claim 1, wherein in the first positions, the first cavity and the second cavity are connected in parallel with the first bore for entrance of the first and second liquid samples into the first cavity and the second cavity, respectively.

4. An apparatus according to claim 1, wherein the first cavity is positioned in a first sampling member movably positioned in the housing, and the second cavity is positioned in a second sampling member movably positioned in the housing.

5. An apparatus according to claim 1, wherein the first cavity and the second cavity are positioned in a first sampling member movably positioned in the housing.

6. An apparatus according to claim 1, wherein the particle characterization means includes a first electrode in the first mixing chamber and a second electrode in the first collection chamber, the first and second electrodes being electrically connected to respective terminal members accessible at the outer surface of the housing.

7. An apparatus according to claim 1, wherein the housing further comprises a first liquid storage chamber for holding a liquid and that, in the second position of the first cavity, communicates with the first cavity so that the liquid can be discharged from the first liquid storage chamber through the first cavity and into the first mixing chamber together with the first liquid sample.

8. An apparatus according to claim 7, wherein the housing further comprises a second liquid storage chamber for holding a liquid and that, in the second position of the second cavity, communicates with the second cavity so that the liquid can be discharged from the second liquid storage chamber through the second cavity and into the first mixing chamber together with the second liquid sample.

9. An apparatus according to claim 8, wherein the housing is a cartridge, the apparatus further comprising:
    a docking station for removably receiving the cartridge,
    the cartridge including a first port communicating with the first mixing chamber for causing liquid flow from the liquid storage chambers through the first cavity and the second cavity to the first mixing chamber, and
    the docking station including a second port for forming a gas connection with the first port when the cartridge is received in the docking station for application of a pressure causing the liquid flow through the first cavity and the second cavity.

10. An apparatus according to claim 9, wherein
    the cartridge further comprises a third port communicating with the first collection chamber for causing liquid flow through the opening, and
    the docking station further comprises a fourth port for forming a gas connection with the third port when the cartridge is received in the docking station for application of a pressure causing the liquid flow through the opening.

11. An apparatus according to claim 1, comprising volume metering means for determining a beginning and an end of at least one period during which a predetermined volume of liquid has passed through the opening.

12. An apparatus according to claim 11, wherein the volume metering means comprises a first volume metering chamber with an input communicating with the collection chamber and an output, and wherein presence of liquid is detected at the input and at the output, respectively.

13. An apparatus according to claim 11, wherein the volume metering means comprises a second volume metering chamber with an input communicating with the output of the first metering chamber and an output, and wherein presence of liquid is detected at the input and at the output of the second volume metering chamber, respectively.

14. An apparatus according to claim 11, wherein presence of liquid is detected optically.

15. An apparatus according to claim 1, further comprising an overflow chamber for accommodation of liquid after passage through the opening.

16. An apparatus according to claim 1, wherein at least one of the first cavity and the second cavity has an anti-coagulation reagent on surfaces thereof.

17. An apparatus according to claim 1, wherein a mixing member is positioned in the first mixing chamber.

18. An apparatus according to claim 17, wherein the mixing member is magnetic.

19. An apparatus according to claim 1, wherein the housing includes a window for spectrophotometric characterization.

20. An apparatus according to claim 1, wherein the housing further comprises a pump chamber communicating with the first collection chamber, and a pump actuator for causing a liquid flow through the opening.

21. An apparatus according to claim 20, wherein the pump actuator is a piston.

22. An apparatus according to claim 20, wherein the pump actuator is a membrane.

23. An apparatus according to claim 1, wherein the housing is a cartridge, and the apparatus further comprises:
  a docking station for removably receiving the cartridge, the docking station including connectors for operational connection with the particle characterization means when the cartridge is received in the docking station.

24. An apparatus for characterizing particles in liquid, comprising a housing with
  a first mixing chamber and a first collection chamber separated by a wall containing an opening for passage of the particles between the first mixing chamber and the first collection chamber,
  particle characterization means for characterizing particles passing through the opening,
  a first bore in the outer surface of the housing for entrance of liquid samples,
  a first cavity for receiving and holding a first liquid sample, the first cavity being movably positioned in relation to the housing, and
  a second cavity for receiving and holding a second liquid sample, the second cavity being movably positioned in relation to the housing in such a way that, in a first position, the second cavity is in communication with the first bore for entrance of the second liquid sample into the second cavity, and, in a second position, the second cavity is in communication with the first mixing chamber for discharge of the second liquid sample into the first mixing chamber,
  wherein the first cavity in a first position is in communication with a second bore in the outer surface of the housing for entrance of the first liquid sample into the first cavity, and, in a second position, the first cavity is in communication with the first mixing chamber for discharge of the first liquid sample into the first mixing chamber.

25. An apparatus according to claim 24, wherein the first cavity is positioned in a first sampling member movably positioned in the housing, and the second cavity is positioned in a second sampling member movably positioned in the housing.

26. An apparatus according to claim 24, wherein the particle characterization means includes a first electrode in the first mixing chamber and a second electrode in the first collection chamber, the first and second electrodes being electrically connected to respective terminal members accessible at the outer surface of the housing.

27. An apparatus according to claim 24, wherein the housing further comprises a first liquid storage chamber for holding a liquid and that, in the second position of the first cavity, communicates with the first cavity so that the liquid can be discharged from the first liquid storage chamber through the first cavity and into the first mixing chamber together with the first liquid sample.

28. An apparatus according to claim 27, wherein the housing further comprises a second liquid storage chamber for holding a liquid and that, in the second position of the second cavity, communicates with the second cavity so that the liquid can be discharged from the second liquid storage chamber through the second cavity and into the first mixing chamber together with the second liquid sample.

29. An apparatus according to claim 24, comprising volume metering means for determining a beginning and an end of at least one period during which a predetermined volume of liquid has passed through the opening.

30. An apparatus according to claim 24, wherein the housing is a cartridge, and the apparatus further comprises:
  a docking station for removably receiving the cartridge, the docking station including connectors for operational connection with the particle characterization means when the cartridge is received in the docking station.

* * * * *